(12) United States Patent
Dees et al.

(10) Patent No.: US 7,402,299 B2
(45) Date of Patent: *Jul. 22, 2008

(54) INTRACORPOREAL MEDICAMENTS FOR PHOTODYNAMIC TREATMENT OF DISEASE

(75) Inventors: H. Craig Dees, Knoxville, TN (US);
Timothy C. Scott, Knoxville, TN (US);
Eric A. Wachter, Oak Ridge, TN (US);
Walter G. Fisher, Knoxville, TN (US);
John Smolik, Loudon, TN (US)

(73) Assignee: Provectus Pharmatech, Inc., Knoxville, TN (US)

( * ) Notice: Subject to any disclaimer, the term of this patent is extended or adjusted under 35 U.S.C. 154(b) by 306 days.

This patent is subject to a terminal disclaimer.

(21) Appl. No.: 10/999,313

(22) Filed: Nov. 30, 2004

(65) Prior Publication Data

US 2005/0154049 A1 Jul. 14, 2005

Related U.S. Application Data

(60) Division of application No. 09/799,785, filed on Mar. 6, 2001, and a continuation-in-part of application No. 09/072,407, filed on May 4, 1998, now Pat. No. 6,042,603, which is a division of application No. 08/739,801, filed on Oct. 30, 1996, now Pat. No. 5,829,448, application No. 10/999,313, which is a continuation-in-part of application No. 09/130,041, filed on Aug. 6, 1998, now abandoned, and a continuation-in-part of application No. 09/184,388, filed on Nov. 2, 1998, now Pat. No. 6,493,570, and a continuation-in-part of application No. 09/216,787, filed on Dec. 21, 1998, now Pat. No. 6,331,286.

(60) Provisional application No. 60/191,803, filed on Mar. 24, 2000, provisional application No. 60/149,015, filed on Aug. 13, 1999.

(51) Int. Cl.
*A61B 5/55* (2006.01)

(52) U.S. Cl. ............... 424/9.37; 424/1.11; 424/1.13; 424/1.17; 424/1.33; 424/1.37; 424/1.57; 424/1.85; 424/9.2; 424/7.37; 424/9.4; 424/9.45; 436/35; 436/57; 436/58; 436/63; 436/64; 436/125

(58) Field of Classification Search ............... 424/1.11, 424/1.13, 1.17, 1.29, 1.33, 1.53, 1.73, 1.85, 424/9.2, 9.4, 9.37, 1.37, 1.57, 9.45; 436/57, 436/58, 63, 64, 829, 35, 125

See application file for complete search history.

(56) References Cited

U.S. PATENT DOCUMENTS 4,490,543 A    12/1984   Bergquist et al.

(Continued)

FOREIGN PATENT DOCUMENTS

EP    0 064 012   * 11/1982

(Continued)

OTHER PUBLICATIONS

Neckers D., Rose Bengal, Journal of Photochemistry and Photobiology, A: Chemistry 47: 1-29 (1989).*

(Continued)

*Primary Examiner*—Gailene R. Gabel
(74) *Attorney, Agent, or Firm*—Cook, Alex, McFarron, Manzo, Cummings & Mehler, Ltd.

(57) ABSTRACT

New intracorporeal photodynamic medicaments and certain medical uses and methods for use of such photodynamic medicaments for treatment of disease in human or animal tissue are described, wherein a primary active component of such medicaments is a halogenated xanthene or halogenated xanthene derivative. In preferred embodiments, such medicaments are used for treatment of a variety of conditions affecting the skin and related organs, the mouth and digestive tract and related organs, the urinary and reproductive tracts and related organs, the respiratory tract and related organs, the circulatory system and related organs, the head and neck, the endocrine and lymphoreticular systems and related organs, various other tissues, such as connective tissues and various tissue surfaces exposed during surgery, as well as various tissues exhibiting microbial or parasitic infection. In another preferred embodiment, such medicaments are produced in various formulations including liquid, semisolid, solid or aerosol delivery vehicles.

2 Claims, 2 Drawing Sheets

U.S. PATENT DOCUMENTS

| | | | |
|---|---|---|---|
| 4,599,227 A | 7/1986 | Dees et al. | 424/38 |
| 4,647,578 A | 3/1987 | Crounse et al. | |
| 4,846,789 A * | 7/1989 | Heitz et al. | 604/522 |
| 4,957,481 A | 9/1990 | Gatenby | 604/20 |
| 4,973,848 A | 11/1990 | Kolobanov et al. | 250/458.1 |
| 5,053,006 A | 10/1991 | Watson | 604/52 |
| 5,128,139 A | 7/1992 | Brown et al. | 424/450 |
| 5,149,801 A | 9/1992 | Kahl et al. | 540/145 |
| 5,177,073 A * | 1/1993 | Gulliya et al. | 514/224.8 |
| 5,284,831 A | 2/1994 | Kahl et al. | 514/21 |
| 5,573,773 A | 11/1996 | Kis et al. | 424/423 |
| 5,576,013 A * | 11/1996 | Williams et al. | 424/423 |
| 5,591,422 A | 1/1997 | Hemmi et al. | 424/362 |
| 5,654,423 A | 8/1997 | Kahl et al. | 540/145 |
| 5,827,186 A | 10/1998 | Chen et al. | 600/407 |
| 5,829,448 A | 11/1998 | Fisher et al. | 128/898 |
| 5,832,931 A | 11/1998 | Wachter et al. | 128/898 |
| 5,998,597 A | 12/1999 | Fisher et al. | 536/23.1 |
| 6,036,941 A * | 3/2000 | Bottiroli et al. | 424/9.6 |
| 6,042,603 A | 3/2000 | Fisher et al. | 607/89 |
| 6,331,286 B1 | 12/2001 | Dees et al. | |
| 2007/0010575 A1* | 1/2007 | Dees et al. | 514/454 |

FOREIGN PATENT DOCUMENTS

| | | |
|---|---|---|
| EP | 0 175 617 | 9/1985 |
| JP | 06-128128 * | 5/1994 |
| WO | WO 96/07431 | 3/1996 |
| WO | WO 97/03697 | 2/1997 |
| WO | WO 97/26920 | 7/1997 |
| WO | WO 97/39064 | 10/1997 |
| WO | WO 00/25665 | 5/2000 |
| WO | WO 00/25819 | 5/2000 |
| WO | WO 00/25829 | 5/2000 |
| WO | WO 00/37927 | 6/2000 |

OTHER PUBLICATIONS

Serafini et al., Iodine 123-Rose Bengal: An Improved Hepatobiliary Imaging Agent, Journal of Nuclear Medicine: 16 (7): 629-632 (1975).*

Xanthenes: Fluorone Derivatives, The Journal of Organic Chemistry 57(1992) Jul. 31, No. 16, Washington, DC pp. 4418-4421.

(Svensk Farmaceutisk Tidskrift (1973) 77 (13): 641-647 (Abstract).

Z. Diwu and J.W. Lown, "Phototherapeutic potential of alternative photosensitizers to porphyrins," Pharmac. Ther., 63 (1994) 1-35.

J.R. Heitz and W.W. Wilson, "Photodegradation of halogenated xanthene dyes," Mississippi Agriculture and Forestry Experiment Station (MAFES), Publication 8532, 35-48.

K. Kalka, H. Merk, and H. Mukhtar, "Photodynamic therapy in dermatology," J.Am. Acad. Derm., 42 (2000) 389-413.

H. Von Tappeiner and A. Jesionek, "Therapeutische versuche mit fluoreszierenden Stoffen (Therapeutic experiments with flourescent substances)", Munch. Med. Wochenschr., 47 (1903) 2042-2044.

U.S. Appl. No. 09/096,832 (pending) to Wachter, et al. filed Jun. 12, 1998, including specification, claims abstract drawings and PTO filing receipt.

Search Report re: PCT/US01/08924. Dated Jun. 22, 2001.

Young, S. et al, "Gadolinium(III) Texaphyrin: A Tumor Selective Radiation Sensitizer that is Detectable by MRI," Proc. Natl. Acad. Sci., vol. 93, pp. 6610-6615, Jun. 1996.

Bernhard, E.J. et al, "Re-Evaluating Gadolinium(III) Texaphyrin as a Radiosensitizing Agent," Cancer Research, vol. 60, pp. 86-91, Jan. 1, 2000.

Fisher et al., "Clinical and Preclinical Photodynamic Therapy", *Lasers In Surgery and Medicine*, vol. 17, p. 2-31, 1995.

Springer-Verlang Berlin Heidelberg 1996; Library of Congress Cataloging-in-Publication Data applied for, pp. 46-85. Laser-Tissue Interactions Fundamental and Applications by Markolf H. Niemz.

Journal of PHotochemistry and Photobiology, A: Chemistry, 47 (1989) pp. 1-29. Rose Bengal by D. C. Neckers.

Supplementary Partial European Search Report dated Mar. 31, 2004.

U.S. Appl. No. 11/124,654, filed May 9, 2005.
U.S. Appl. No. 09/635,276, filed Aug. 9, 2000.
U.S. Appl. No. 09/799,785, filed Mar. 6, 2001.
U.S. Appl. No. 09/817,448, filed Mar. 26, 2001.
U.S. Appl. No. 10/331,854, filed Dec. 30, 2002.
U.S. Appl. No. 09/900,355, filed Feb. 6, 2001.

* cited by examiner

INTRACORPOREAL MEDICAMENTS FOR PHOTODYNAMIC TREATMENT OF DISEASE

CROSS-REFERENCE TO RELATED APPLICATIONS

This application is a divisional of co-pending application U.S. Ser. No. 09/799,785 filed Mar. 6, 2001 which is based on provisional application U.S. Ser. No. 60/191,803 filed Mar. 24, 2000 and is a continuation-in-part of U.S. Ser. No. 09/072,407, filed May 4, 1998 (now U.S. Pat. No. 6,042,603 and entitled "Method for Improved Selectivity in Photo-Activation of Molecular Agents") which is a divisional of application Ser. No. 08/739,801, now U.S. Pat. No. 5,829,448 filed Oct. 30, 1996; U.S. Ser. No. 09/130,041, filed on Aug. 6, 1998 now abandoned (entitled "Improved Method for Targeted Treatment of Disease"); U.S. Ser. No. 09/184,388, filed on Nov. 2, 1998 (now U.S. Pat. No. 6,493,570 and entitled "Method for Improving Imaging and Photodynamic Therapy"); U.S. Ser. No. 09/216,787, filed on Dec. 21, 1998 (now U.S. Pat. No. 6,331,286 and entitled "High Energy Phototherapeutic Agents"); and U.S. Ser. No. 60/149,015, filed on Aug. 13, 1999 (entitled "Improved Topical Medicaments And Methods For Photodynamic Treatment Of Disease"), which are herein incorporated by reference in their entirety.

BACKGROUND OF THE INVENTION

1. Field of the Invention

The present invention is related to certain photodynamic medicaments and methods for treatment of human or animal tissue using photodynamic therapy (PDT). The inventors of the present invention have found that such medicaments are useful for the treatment of a variety of conditions affecting the skin and related organs, the mouth and digestive tract and related organs, the urinary and reproductive tracts and related organs, the respiratory tract and related organs, the circulatory system and related organs, the head and neck, the endocrine and lymphoreticular systems and related organs, various other tissues, such as connective tissues and various tissue surfaces exposed during surgery, as well as various tissues exhibiting microbial, viral, fungal or parasitic infection. These medicaments are available in various formulations that may include liquid, semisolid, solid or aerosol delivery vehicles, and are suitable for intracorporeal administration via various conventional modes and routes, including intravenous injection (i.v.), intraperitoneal injection (i.p.), intramuscular injection (i.m.), intracranial injection (i.c.), intratumoral injection (i.t.), intraepithelial injection (i.e.), transcutaneous delivery (t.c.), and per oesophageal (p.o.) administration. These photoactive ingredients contain intracorporeal medicaments, the photoactivation of which produces a desirable therapeutic response, such as destruction of microbial infection, reduction or elimination of tissue irritation, reduction or elimination of hyperproliferative tissue, reduction or elimination of cancerous or precancerous tissue, reduction or elimination of surface or subsurface lipocytes or lipid deposits, and many other similar indications.

2. Description of the Related Art

PDT was originally developed to treat cancer and other diseases with the promise of limiting the invasiveness of the therapeutic intervention and lessening potential collateral damage to normal, non-diseased tissue. In its simplest form, PDT is the combination of a photosensitive agent with special forms of illumination to produce a therapeutic response in certain tissues, such as a tumor. The agent attains an excited, active state when it absorbs one or more photons, and then is or becomes efficacious. Key elements of a successful PDT regimen include either selective application or selective uptake of a photosensitive agent into the diseased tissue and site-specific application of the activating light. PDT agents are typically applied systemically (for example, via intravenous injection or oral administration) or via localized topical application directly to diseased tissues (for example, via topical creams, ointments, or sprays). Subsequent to administration of the agent (typically 30 minutes to 72 hours later), activating light is applied to the disease site, locally activating the agent, and destroying the diseased tissue. Light is typically applied by direct illumination of the site, or by delivery of light energy to internal locations using a fiberoptic catheter or similar approach.

Most current PDT regimens are based on systemic application of porphyrin-based agents or topical or systemic application of psoralen-based agents. Examples of porphyrin-based agents include porfimer sodium (PHOTOFRIN®), hematoporphyrin-derivative (HPD), benzoporphyrin derivative (BPD), Lutex, BOPP and $SnET_2$. PHOTOFRIN® is one of the few agents currently licensed by the U.S. FDA. Porphyrin-based agents generally are derived from complex mixtures of natural or synthetically prepared materials and may contain components that are lipophilic. As a possible result of this lipophilicity, porphyrin-based agents have shown a slight tendency to accumulate preferentially in some tumors and other diseased tissues. However, the targeting of such agents to diseased tissue is still unacceptably low when compared to uptake in normal tissue, (i.e., at most 2-10× greater uptake in diseased tissue relative to normal tissue). The psoralens, such as 8-MOP, 5-MOP, trioxsalen, and AMT, are nucleic acid intercalators that function by disrupting cell regulation or impairing cellular physiology upon photoactivation. This mechanism of action appears to be relatively indiscriminate in terms of tissue type, and as a result these agents also exhibit minimal specificity for diseased tissue. Thus, current PDT agents have not exhibited high specificity and may exhibit additional disadvantages, including persistent systemic or localized photosensitivity, systemic or localized toxicity, and high treatment cost (due to high agent cost or excessive dosage requirements).

Consequently, PDT has not become widespread, given these background problems of target specificity and cost of treatment.

Therefore, it is an object of the present invention to provide new medicaments, new medical uses for such medicaments based on improved specificity of such medicaments for the desired target tissue to be treated, and methods for treatment using such medicaments, thereby resulting in improved treatment outcomes, increased efficacy and safety and reduced cost of treatment.

SUMMARY OF THE PRESENT INVENTION

The present invention is directed to new intracorporeal photodynamic medicaments and certain medical uses of such medicaments, and methods for treatment using such medicaments, for treatment of human or animal tissue, wherein a primary active component of such medicaments is a halogenated xanthene or a halogenated xanthene derivative, and more preferably Rose Bengal or a functional derivative of Rose Bengal. The halogenated xanthenes constitute a family of potent photosensitizers that become photoactivated upon illumination of the treatment site with visible wavelengths of light. Such medicaments are suitable for intracorporeal administration, and are thus intracorporeal medicaments. Such medicaments can also be called pharmaceutical compositions or agents.

In a preferred embodiment, such medicaments are used for photodynamic treatment of a variety of conditions affecting the skin and related organs.

In another preferred embodiment, such medicaments are used for photodynamic treatment of a variety of conditions affecting the mouth and digestive tract and related organs.

In another preferred embodiment, such medicaments are used for photodynamic treatment of a variety of conditions affecting the urinary and reproductive tracts and related organs.

In another preferred embodiment, such medicaments are used for photodynamic treatment of a variety of conditions affecting the respiratory system and related organs.

In another preferred embodiment, such medicaments are used for photodynamic treatment of a variety of conditions affecting the circulatory system and related organs.

In another preferred embodiment, such medicaments are used for photodynamic treatment of a variety of conditions affecting the head and neck.

In another preferred embodiment, such medicaments are used for photodynamic treatment of a variety of conditions affecting the endocrine and lymphoreticular systems and related organs.

In another preferred embodiment, such medicaments are used for photodynamic treatment of a variety of conditions affecting various other tissues, such as connective tissues and various tissue surfaces exposed during surgery.

In another preferred embodiment, such medicaments are used for photodynamic treatment of a variety of conditions related to microbial or parasitic infection.

In another preferred embodiment, such medicaments are produced in various formulations including liquid, semisolid, solid or aerosol delivery vehicles, as well as in tablet, capsule, suppository, and other similar forms.

BRIEF DESCRIPTION OF THE DRAWINGS

In describing the preferred embodiments, reference is made to the accompanying drawings wherein.

DETAILED DESCRIPTION OF THE PRESENTLY PREFERRED EMBODIMENTS

Figure 1A:
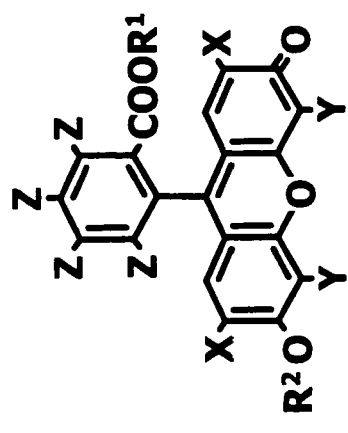
FIG. 1(a) shows the generalized chemical structure of the halogenated xanthenes.

The present invention is directed to new photodynamic medicaments and certain medical uses of such photodynamic medicaments, and methods for photodynamic treatment using such medicaments, for treatment of human or animal tissue, wherein a primary active component of such medicaments is a halogenated xanthene or halogenated xanthene derivative. The inventors of the present invention have discovered that such halogenated xanthenes, as discussed in more detail infra, exhibit desirable photodynamic effects when applied to or otherwise delivered to certain human or animal tissues. The desirable effects include reduction or elimination of disease or diseased tissue or other undesirable conditions, including eradication of cancerous or pre-cancerous tumors and infectious agents. The treatment is applicable to a variety of conditions affecting the skin and related organs, the mouth and digestive tract and related organs, the urinary and reproductive tracts and related organs, the respiratory tract and related organs, the circulatory system and related organs, the head and neck, the endocrine and lymphoreticular systems and related organs, various other tissues, such as tissues exposed during surgery, as well as various tissues exhibiting microbial, viral, fungal or parasitic infection.

In a preferred embodiment, such medicaments are produced in various formulations suitable for intracorporeal administration, including in various liquid, semisolid, solid or aerosol delivery vehicles, as well as in tablet, capsule, suppository, and other similar forms. Such medicament formulations are suitable for delivery via various conventional modes and routes (hereafter defined as intracorporeal administration), including intravenous injection (i.v.), intraperitoneal injection (i.p.). intramuscular injection (i.m.), intracranial injection (i.c.), intratumoral injection (i.t.), intraepithelial injection (i.e.), transcutaneous delivery (t.c.), and per oesophageal (p.o.) administration; additional administrative modes and routes include intraabdominal, intraappendicular, intraarterial, intraarticular, intrabronchial, intrabuccal, intracapsular, intracardial, intracartilaginous, intracavitary, intracephalic, intracolic, intracutaneous, intracystic, intradermal, intraductal, intraduodenal, intrafascicular, intrafat, intrafilar, intrafissural, intragastric, intraglandular, intrahepatic, intraintestinal, intralamellar, intralesional, intraligamentous, intralingual, intramammary, intramedullary, intrameningeal, intramyocardial, intranasal, intraocular, intraoperative, intraoral, intraosseous, intraovarian, intrapancreatic, intraparietal, intrapelvic, intrapericardial, intraperineal, intraperitoneal, intraplacental, intrapleural, intrapontine, intraprostatic, intrapulmonary, intrarachidian, intrarectal, intrarenal, intrascleral, intrascrotal, intrasegmental, intrasellar, intraspinal, intrasplenic, intrasternal, intrastromal, intrasynovial, intratarsal, intratesticular, intrathoracic, intratonsillar, intratracheal, intratubal, intratympanic, intraureteral, intraurethral, intrauterine, intravaginal, intravascular, intraventricular, intravertebral, intravesical, or intravitreous administration. Such medicaments will thus be referred to as intracorporeal medicaments (i.e., medicaments suitable for intracorporeal administration).

1. Properties of the Preferred Photoactive Components and Medicament Formulations.

The inventors of the present invention have discovered a class of photoactive agents that are broadly applicable for producing intracoporeal medicaments for photodynamic treatment of disease in certain human and animal tissues. These photoactive agents are referred to as halogenated xanthenes and are illustrated in FIG. 1a, where the symbols X, Y, and Z represent various elements present at the designated positions, and the symbols $R^1$ and $R^2$ represent various functionalities present at the designated positions.

Selected chemical and physical properties (such as chemical constituents at positions X, Y, and Z and functionalities $R^1$ and $R^2$, along with molecular weight and photochemical characteristics) of representative halogenated xanthenes are summarized in attached Table 1. Certain general properties of this class of agents are discussed in further detail in U.S. Ser. No. 09/130,041, filed on Aug. 6, 1998, U.S. Ser. No. 09/184, 388, filed on Nov. 2, 1998, and U.S. Ser. No. 09/216,787, filed on Dec. 21, 1998, which are herein incorporated by reference in their entirety. In general, the halogenated xanthenes are characterized by a low dark cytotoxicity (toxicity to cells or tissues in the absence of photoactivation), by high light cytotoxicity (toxicity to cells or tissues upon photoactivation) and by chemical and photochemical properties that are substantially unaffected by the local chemical environment or by the attachment of functional derivatives at positions $R^1$ and $R^2$. Such factors make these chemical agents, and in particular intracorporeal medicaments formulated from such agents, excellent PDT agents for the treatment of disease in human and animal tissues.

Figure 1B:
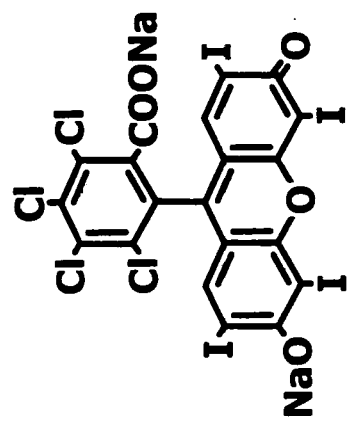
FIG. 1(b) shows the chemical structure of Rose Bengal.

One preferred embodiment of an intracorporeal medicament according to the present invention contains an active ingredient, at a concentration of from greater than approximately 0.001% to less than approximately 20%, of at least one halogenated xanthene, including for example one or more of: Fluorescein; 4',5'-Dichlorofluorescein; 2',7'-Dichlorofluorescein; 4,5,6,7-Tetrachlorofluorescein; 2',4',5',7'-Tetrachlorofluorescein; Dibromofluorescein; Solvent Red 72; Diiodofluorescein; Eosin B; Eosin Y; Ethyl Eosin; Erythrosin B; Phloxine B; Rose Bengal; 4,5,6,7-Tetrabromoerythrosin; Mono-, Di-, or Tribromoerythrosin; Mono-, Di-, or Trichloroerythrosin; Mono-, Di-, or Trifluoroerythrosin; 2',7'-Dichloro-4,5,6,7-Tetrafluorofluorescein; 2',4,5,6,7,7'-Hexafluorofluorescein; and 4,5,6,7-Tetrafluorofluorescein. It is further preferred that this medicament include Rose Bengal (4.5.6,7-tetrachloro-2',4',5',7'-Tetraiodofluorescein, illustrated in FIG. 1b).

Figure 2:
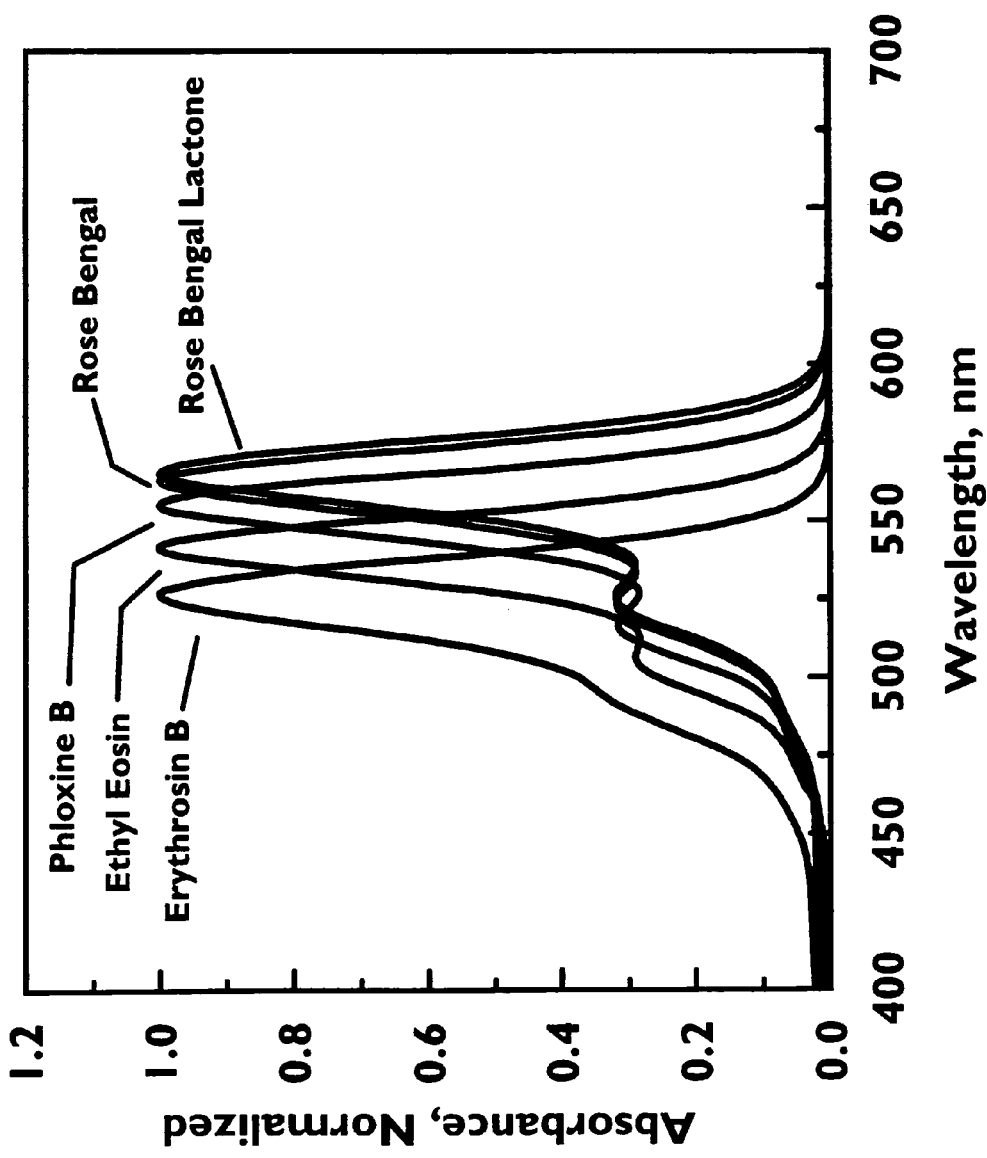
FIG. 2 shows example absorbance spectra of several halogenated xanthenes.

Further, as evidenced by the data shown in Table 1 (infra) and in FIG. 2, halogenated xanthenes share common spectroscopic properties, including a high single-photon cross-section extending from approximately 500 nm to 600 nm. These properties are substantially invariant regardless of state of functional derivatization (for example, at positions $R^1$ and $R^2$) or of chemical or biological environment. This feature facilitates photoactivation with commonly available visible light sources operating in the band from approximately 500 nm to 600 nm and circumvents the need to substantively change sources if the specific photoactive component of the medicament is varied or modified, as discussed herein. Furthermore, the inventors of the present invention have shown that the halogenated xanthenes are capable of being activated using non-linear, multi-photon excitation under certain conditions when using light in the near infrared band from approximately 700 nm to 1200 nm (using methods such as, for example, those taught in U.S. Pat. No. 6,042,603 and in U.S. Ser. No. 09/096,832, filed Jun. 12, 1998 (entitled "Improved Methods And Apparatus For Multi-Photon Photo-Activation Of Therapeutic Agents"), both of which is incorporated herein by reference in their entireties). Such excitation methods provide additional utility in the activation of medicaments formulated from these agents, for example when it is desirable to increase the depth of photoactivation to positions substantially beyond that readily accessible using visible light excitation methods.

As an example of these desirable chemical, biochemical, and physical properties, the inventors have found that the prototypical halogenated xanthene, Rose Bengal, will accumulate preferentially in (i.e. target) some tumors and other tissues and pathogenic entities, has negligible dark cytotoxicity, high light cytotoxicity upon illumination with visible light, relatively low cost, and the ability to clear rapidly from the body.

For example, it is possible to estimate an agent's potential for tissue accumulation based on the partition coefficient, $K_p$. This in vitro parameter is purported to have predictive value relating to in vivo agent delivery at the cellular level. In particular, a value greater than unity is considered to indicate agents capable of localizing in tumor or other diseased tissue, and more specifically in plasma membranes of cells composing such tissue, and thereby being capable of exhibiting enhanced photodynamic efficacy in such tissue. $K_p$ is determined by measuring the ratio of equilibrium concentrations of an agent in a lipophilic phase (n-octanol) contacted with an aqueous phase (phosphate buffered saline, PBS, pH=7.4). Comparative values of $K_p$ are shown in Table 2. infra. The large $K_p$ values for the halogenated xanthenes relative to many of the porphyrin-based PDT agents suggest that the halogenated xanthenes will exhibit an enhanced tendency to concentrate or accumulate in tumor or other diseased tissue, and should thereby be capable of exhibiting superior photodynamic efficacy in such tissue.

The following examples illustrate this preference for accumulation in tumor tissue by the halogenated xanthenes:

Initially, tumor cell suspensions (e.g. melanoma, breast tumor, liver tumor, renal carcinoma, gall bladder tumor or prostate tumor) were injected subcutaneously into the flanks of nude mice resulting in formation of primary tumors, within a few weeks, at the injection site having a volume of approximately 0. 1 $cm^3$ to 0.5 $cm^3$.

Thereafter, a solution of Rose Bengal (10-30 μL of 10% Rose Bengal, i.e., 1-3 mg Rose Bengal p.o.) was administered per oesophageal to the mice, followed by illumination of the tumor 3-48 hours post administration using light at 532 nm (50-200 J/$cm^2$ at the tumor surface). This resulted in selective destruction of tumor tissue with no substantive effect in healthy surrounding tissue. These example results are summarized in Table 3, infra.

Intratumoral injection (i.t.) of a similar Rose Bengal formulation resulted in persistent accumulation and retention of Rose Bengal uniformly throughout the tumor volume, with more than 75% of injected Rose Bengal dose remaining in the tumor after several weeks. As in the per oesophageal example above, illumination using light at 532 nm resulted in selective tumor destruction (see Table 4, infra).

Peritumoral injection (i.e., injection into normal tissue around the outside margins of the tumor) exhibited no such retention in normal tissue, with less than 1% of Rose Bengal remaining in the vicinity of the tumor after 24 hours.

In contrast, i.t. administration of a different class of agent indocyanine green ($K_p$=99), showed that within 24 hours this agent had substantively migrated out of the tumor, and instead exhibited a tendency to accumulate in peritumoral tissues. Hence, while the $K_p$ value for indocyanine green is nearly ten-fold larger than that of Rose Bengal (and as such, indocyanine green is, by the conventional model based on $K_p$, expected to accumulate strongly in tumor tissue), the tissue localization properties of the two agents are clearly completely different.

Thus, the inventors of the present invention have shown that the halogenated xanthenes, and in particular Rose Bengal, exhibit an unexpectedly marked preference for accumulation and retention in tumor and other diseased tissue upon intracorporeal administration, and that once present in such tissue, said halogenated xanthenes can be utilized as potent, highly tissue or disease specific PDT agents.

In addition to superior suitability for direct administration into desired targeted tissue to be treated, such as a focal tumor, the preference of the halogenated xanthenes for accumulation in certain types of tissues provides a basis for highly-selective, systemic delivery of the halogenated xanthenes to such tissues. For example, Rose Bengal's relatively large partition coefficient is indicative of a preference for accumulation in lipophilic tissue, such as cutaneous lipocytes. The inventors of the present invention have found that systemic administration of Rose Bengal, for example as an aqueous solution administered via intraperitoneal injection (i.p.) or per oesophagus (p.o.) administration, resulted in highly selective accumulation of said agent in certain tissues, such as in the cutaneous fat deposits of obese laboratory mice. Histologic examination of skin samples from such animals showed that accumulated agent is substantively limited to cutaneous lipocytes. Furthermore, illumination of the skin of such animals with light at approximately 532 nm resulted in photodynamic activation of this accumulated agent only in such lipocytes. Such photodynamic activation of accumulated agent precipitated selective photodynamic destruction of such lipocytes with no effect in overlying skin or underlying muscle tissue.

Moreover, the inventors of the present invention have discovered that the facility with which the halogenated xanthenes target specific tissues or other sites can be further optimized by attachment of specific functional derivatives at positions $R^1$ and $R^2$ (see e.g. FIG. 1), so as to change the chemical partitioning and/or biological activity of the agent. For example, attachment of one targeting moiety or more at positions $R^1$ or $R^2$ can be used to improve targeting to specific tissues, such as cancerous tumor tissues or sites of localized infection. An example of this is esterification at position $R^1$ with a short aliphatic alcohol, such as n-hexanol, to produce a derivatized agent exhibiting enhanced partitioning into lipid-rich tumor tissues.

It is thus a further preferred embodiment to include a targeting moiety in at least one of the at least one halogenated xanthene active ingredients, such targeting moiety being selected from a group that includes deoxyribonucleic acid (DNA), ribonucleic acid (RNA), amino acids, proteins, antibodies, ligands, haptens, carbohydrate receptors, carbohydrate complexing agents, lipid receptors, lipid complexing agents, protein receptors, protein complexing agents, chelators, encapsulating vehicles, short-chain aliphatic hydrocarbons, long-chain aliphatic hydrocarbons, aromatic hydrocarbons, aldehydes, ketones, alcohols, esters, amides, amines, nitriles, azides, hydrophilic moieties and hydrophobic moieties. A further example of this embodiment is derivatization of Rose Bengal with a lipid (at position $R^1$, via esterification), so as to increase the lipophilicity of Rose Bengal, and thereby modify its targeting properties in a patient. An additional further example of this embodiment is derivatization of Rose Bengal with folate (at position $R^1$, via esterification or other modes of attachment), so as to increase selective targeting of cancer and other cells exhibiting enhanced folate receptor activity or folate metabolism.

As a further example of the desirable chemical, biochemical, and physical properties of the halogenated xanthenes and halogenated xanthene derivatives, the inventors of the present invention have shown that these agents exhibit a remarkable combination of low dark cytotoxicity and high light cytotoxicity. This is evidenced by the following: addition of Rose Bengal and other halogenated xanthenes to procaryotic or eucaryotic cell cultures at concentrations equivalent to or greater than 100 mg/kg generally resulted in no measurable effect on the viability of such cultures. However, subsequent illumination of such cultures with light at wavelengths between about 500 nm and 600 nm generally resulted in an immediate and complete kill of such cell cultures. Intracorporeal administration of these agents at these levels into tumor-bearing laboratory animals resulted in negligible biological effects in the absence of illumination. However, illumination of tumor tissue in these animals subsequent to this administration resulted in marked destruction of such tumor tissue. Further, the inventors of the present invention have shown that these agents are readily cleared from healthy tissues in a matter of several hours and are known to be rapidly excreted in bile, urine and feces, without doing damage to those healthy tissues while it was there. This is in dramatic contrast to most conventional PDT agents, some of which exhibit half-lives in healthy tissues on the order of many weeks.

Further examples of the desirable properties of the halogenated xanthenes and halogenated xanthene derivatives are as follows: halogenated xanthenes and halogenated xanthene derivatives are easily synthesized using simple, low-cost synthetic methods, can be readily purified and exhibit excellent stability (such as a long shelf life without need for refrigeration or storage under an inert atmosphere).

Because the halogenated xanthenes and their derivatives are, in general, fine solid powders in their pure form, it is preferred that, for proper delivery to desired tissues, such agents be formulated in appropriate delivery vehicles. Approaches to such formulation will be generally known to those of ordinary skill in the art. Specifically, such formulations are preferred so as to facilitate agent delivery into the body and subsequent contact with, and delivery to, desired tissues to be treated.

It is thus a further preferred embodiment of the present invention that at least one halogenated xanthene or halogenated xanthene derivative be formulated as an intracorporeal medicament in a form suitable for intracorporeal administration via various conventional modes and routes. Such suitable forms include, for example, medicaments formulated in a liquid, semisolid, solid or aerosol delivery vehicle, including in vehicles of the following natures: aqueous suspensions, non-aqueous suspensions, solutions, creams, ointments, gels, syrups, micro-droplet sprays, suppositories, tablets and capsules. The at least one halogenated xanthene or halogenated xanthene derivative may be dissolved or suspended in such delivery vehicle, wherein this vehicle may, in addition to the at least one halogenated xanthene or halogenated xanthene derivative, include various builders, stabilizers, emulsifiers or dispersants, preservatives, buffers, electrolytes, and tissue penetrating or softening agents. Such components of the delivery vehicle may be present as the primary component (by weight or volume) of the medicament, or as a minor component that serves in an adjuvant role in agent delivery with no adverse affect on tissue or treatment outcome.

For example, appropriate builders include cellulose and cellulose derivatives, such as starch, methylcellulose, carboxymethylcellulose, and alginates.

Examples of appropriate stabilizers, emulsifiers or dispersants include liposomes, nanoparticulates and nanodispersions, microparticulates and microdispersions, as well as various lipids, detergents and other surfactants.

Examples of appropriate preservatives include benzalkonium chloride, thimerosal, quaternary amines and urea.

Examples of appropriate buffers include monobasic or dibasic phosphate salts, citrate salts, bicarbonate salts, and ethanolamine.

Examples of appropriate electrolytes include sodium, potassium, calcium and magnesium chlorides, phosphates, and nitrates.

Examples of appropriate tissue penetrating, softening or solvating agents and adjuvants include:
  various sulfoxides, such as DMSO and decylmethylsulfoxide;
  various aliphatic and fatty alcohols, such as ethanol, propanol, hexanol, octanol, benzyl alcohol, decyl alcohol, lauryl alcohol, and stearyl alcohol;
  various linear and branched, saturated and unsaturated fatty acids, such as lauric acid, caproic acid, capric acid, myristic acid, stearic acid, oleic acid, isovaleric acid, neopentanoic acid, trimethyl hexanoic acid, neodecanoic acid and isostearic acid;

various aliphatic and alkyl fatty acid esters, such as isopropyl n-butyrate, isopropyl n-hexanoate, isopropyl n-decanoate, isopropyl myristate, isopropyl palmitate, octyldodecyl myristate, ethyl acetate, butyl acetate, methyl acetate, methylvalerate, methylpropionate, diethyl sebacate and ethyl oleate;

various polyols, such as propylene glycol, polyethylene glycol, ethylene glycol, diethylene glycol, triethylene glycol, diproplyene glycol, glycerol, propanediol, butanediol, pentanediol and hexanetriol;

various amides, such as urea, dimethylacetamide, diethyltoluamide, dimethylformamide, dimethyloctamide, dimethyldecamide; biodegradable cyclic urea, such as 1-alkyl-4-imidazolin-2-one; pyrrolidone derivatives, such as 1-methyl-2-pyrrolidone, 2-pyrrolidone, 1-lauryl-2-pyrrolidone, 1-methyl-4-carboxy-2-pyrrolidone, 1-hexyl-4-carboxy-2-pyrrolidone, 1-lauryl-4-carboxy-2-pyrrolidone, 1-methyl-4-methyoxycarbonyl-2-pyrrolidone, 1-methyl-4-methyoxycarbonyl-2-pyrrolidone, 1-lauryl-4-methyoxycarbonyl-2-pyrrolidone, N-cyclohexylpyrrolidone, N-dimethylaminopropylpyrrolidone, N-cocoalkypyrrolidone, N-tallowalkylpyrrolidone; biodegradable pyrrolidone derivatives, such as fatty acid esters of N-(2-hyroxyethyl)-2-pyrrolidone; cyclic amides, such as 1-dodecylazacycloheptane-2-one (Azone®), 1-geranylazacycloheptan-2-one, 1-farnesylazacycloheptan-2-one, 1-geranylgeranylazacycloheptan-2-one, 1-(3,7-dimethyloctyl)azacycloheptan-2-one, 1-(3,7,11-trimethydodecyl)azacycloheptan-2-one, 1-geranylazacyclohexane-2-one, 1-geranylazacyclopentan-2,5-dione, 1-farnesylazacyclopentan-2-one; hexamethylenelauramide and its derivatives; and diethanolamine and triethanolamine; various surfactants, such as anionic surfactants, including sodium laurate and sodium lauryl sulfate; cationic surfactants, including cetyltrimethyl ammonium bromide, tetradecyl-trimethylammonium bromide, benzalkonium chloride, octadecyltrimethylammonium chloride. cetylpyridinium chloride, dodecyltrimethylammonium chloride, hexadecyltrimethylammonium chloride; nonionic surfactants, such as Polaxamer (231, 182, 184), Brij (30, 93, 96, 99), Span (20, 40, 60, 80, 85), Tween (20, 40, 60, 80,), Myrj (45, 51, 52), Miglyol 840; various bile salts, such as sodium cholate, sodium salts of taurocholic, glycholic, desoxycholic acids; lecithin; various terpenes, including hydrocarbons, such as D-limonene, α-pinene, β-carene; various terpene alcohols, including α-Terpineol, terpinen-4-ol, carvol; various terpene ketones, including carvone, pulegone, piperitone, menthone; various terpene oxides, including cyclohexane oxide, limonene oxide, α-pinene oxide, cyclopentene oxide, 1,8-cineole; various terpene oils, including ylang ylang, anise, chenopodium, eucalyptus;

various alkanones, such as N-heptane, N-octane, N-nonane, N-decane, N-undecane. N-dodecane, N-tridecane, N-tetradecane, N-hexadecane;

various organic acids, such as salicylic acid and salicylites (including their methyl, ethyl, and propyl glycol derivatives), citric and succinic acid.

The present invention is not limited to the above recited examples, as other formulations familiar to those of ordinary skill in the art, including various simple or complex combinations of vehicles and adjuvants, are also useful for improving delivery of the photoactive component of the medicament to target tissues.

2. Methods and Medical Use of the Subject Medicament for Photodynamic Treatment of Conditions Affecting the Skin and Related Organs.

The inventors have discovered that the intracorporeal medicaments disclosed herein are broadly applicable to improved photodynamic treatment of various conditions affecting the skin and related organs of humans and animals. The medicament can be applied, using conventional intracorporeal administration modes, directly or indirectly to, or substantially proximal to, tissues to be treated including those of the skin, nails and scalp. Such administration modes provide direct delivery of medicament to, into or substantially proximal to, tissues to be treated, or systemic delivery of medicament to, into or substantially proximal to, tissues to be treated.

Example indications include treatment for: Psoriasis and Pustular Psoriasis; Reiter's Syndrome; Skin Ulcers, including Stasis Dermatitis, Stasis Ulcers, Ischemic Ulcers, Sickle Cell Leg Ulcers, Diabetic Ulcers, Inflammatory Ulcers; Eczematous Disease and Eczematous Reaction; various Ichthyoses; Atopic Dermatitis; Superficial Wrinkles; Near Surface Fat Reduction; Benign and Malignant Proliferative Disorders, such as Benign Epithelial Tumors and Hamartomas; Premalignant and Malignant Epithelial Tumors, including Actinic Keratoses, Basal Cell Carcinoma, Squamous Cell Carcinoma, and Keratoacanthoma; Benign and Malignant Adnexal Tumors; Tumors of Pigment-Producing Cells, including Malignant Melanoma, Solar Lentigines, Nevi, and Café-au-lait; Sarcomas; Lymphomas; Vascular Disorders, such as Hemangiomas and Port Wine Stain; Microbial Infection, such as Bacterial, Fungal, Yeast, Parasitic or Other Infections; Warts; and Acne. These examples are provided for illustrative purposes, as the present invention is not limited to the recited examples and includes other indications known to those skilled in the art.

In an example of a preferred embodiment of this method of treatment or medical use, the inventors have found that per oesophageal administration of a medicament solution containing Rose Bengal at a concentration of approximately 10% W/V to mice exhibiting cutaneous tumors, followed by illumination of such tumors with green light in the 500-600 nm band, leads to substantial or complete photodynamic eradication of such tumors. The present invention, however, is not limited to this preferred embodiment, as other medicaments disclosed herein can also be used. Further, other formulations of the halogenated xanthenes as described in the present application have similar applications for the specific indications described herein, and for various other similar indications, including those related to therapeutic or cosmetic treatment of the skin and related organs of humans and animals.

3. Methods and Medical Use of the Subject Medicament for Photodynamic Treatment of Conditions Affecting the Mouth and Digestive Tract and Related Organs.

The inventors have discovered that the intracorporeal medicaments disclosed herein are broadly applicable to improved photodynamic treatment of various conditions affecting the mouth and digestive tract and related organs of humans and animals. The medicament can be applied, using conventional intracorporeal administration modes, directly or indirectly to, or substantially proximal to, tissues to be treated, including those of the mouth, gums, tongue, larynx, pharynx, esophagus. stomach intestines and colon. Such administration modes provide direct delivery of medicament to, into or substantially proximal to, tissues to be treated, or systemic delivery of medicament to, into or substantially proximal to, tissues to be treated.

Example indications include treatment for: Benign Esophageal Lesions, Barretts Esophagus and other Esophageal Hyperplasia and Dysplasia, and Esophageal Cancer, including Squamous Cell Carcinoma, Adenocarcinoma, Carsinosarcoma, Pseudosarcoma, and Sarcoma; Gastric Ulcers, Leiomyomas, Polyps, Neoplasms, Lymphoma and Pseudolymphoma, Adenocarcinoma, Primary Lymphoma, Leiomyosarcoma; Oral and Oropharynx Cancer and Premalignancies, Ulcers and Inflammatory Lesions, including Squamous Cell Carcinoma, Lymphoma, Actinic Cheilitis, Nicotine Stomatitis, Leukoplakia, Erythroplakia; Gum and Other Peridontal Disease, including Gingivitis; Laryngeal Hyperplasia, Dysplasia and Neoplasms; Colorectal Cancer and Polyps. These examples are provided for illustrative purposes, as the present invention is not limited to the recited examples and includes other indications known to those skilled in the art.

In an example of a preferred embodiment of this method of treatment or medical use, the inventors have found that per oesophageal administration of a medicament solution containing Rose Bengal at a concentration of approximately 1.0% W/V to canines, followed by illumination of a region of esophageal tissue with green light in the 500-600 nm band, leads to controlled, localized photodynamic destruction of tissues in the treated region. The present invention, however, is not limited to this preferred embodiment, as other medicaments disclosed herein can also be used. Further, other formulations of the halogenated xanthenes as described herein have similar applications for the specific indications described herein, and for various other similar indications, including those related to therapeutic or cosmetic treatment of the mouth and digestive tract and related organs of humans and animals.

4. Methods and Medical Use of the Subject Medicament for Photodynamic Treatment of Conditions Affecting the Urinary and Reproductive Tracts and Related Organs.

The inventors have discovered that the intracorporeal medicaments disclosed herein are broadly applicable to improved photodynamic treatment of various conditions affecting the urinary and reproductive tract and related organs of humans and animals. The medicament can be applied, using conventional intracorporeal administration modes, directly or indirectly to, or substantially proximal to tissues to be treated, including those of the urethra, bladder, ureter, kidneys, vulva, vagina, cervix, uterus, fallopian tubes, ovaries, penis, testes, vas deferens, prostate, and epididymis. Such administration modes provide direct delivery of medicament to, into or substantially proximal to, tissues to be treated, or systemic delivery of medicament to, into or substantially proximal to, tissues to be treated.

Example indications include treatment for: Urinary Tract Disease, including Cancerous and Pre-Cancerous Hyperplasia, Dysplasia and Neoplasms, Tumors and other Growths, Inflammation, and Infection of the Bladder, Ureter, Urethra, and Kidney; Cancerous and Pre-Cancerous Hyperlasia, Dysplasia and Neoplasms, Tumors and other Growths, Inflammation, and Infection of the Cervix, Endometrium, Myometrium, Ovaries, Fallopian Tubes, Uterus, Vulva, and Vagina, including Vaginal Warts; Cancerous and Pre-Cancerous Hyperlasia, Dysplasia and Neoplasms, Tumors and other Growths, Inflammation, and Infection of the Prostate and Testes; Cancerous and Pre-Cancerous Hyperlasia, Dysplasia and Neoplasms, Tumors and other Growths, Inflammation, and Infection of the Breast; Reproductive Tract Infections, including Tinea Cruris, Candidiasis, Condylomata Acuminata, Molluscum Contagiosum, Genital Herpes Simplex Infection, Lymphogranuloma Venereum, Chancroid, Granuloma Inguinale, Erythrasma; Psoriais; and Lichen Planus and Lichen Sclerosus. These examples are provided for illustrative purposes, as the present invention is not limited to the recited examples and includes other indications known to those skilled in the art.

In an example of a preferred embodiment of this method of treatment or medical use the inventors have found that intratumoral injection of a medicament solution containing Rose Bengal at a concentration of approximately 10% W/V into tumor tissue, such as that of a prostate tumor, followed by illumination of said tumor tissue with green light in the 500-600 nm band, leads to controlled, localized photodynamic eradication of such tumors. The present invention, however, is not limited to this preferred embodiment, as other medicaments disclosed herein can also be used. Further, other formulations of the halogenated xanthenes as described herein have similar applications for the specific indications described herein, and for various other similar indications, including those related to therapeutic or cosmetic treatment of the urinary and reproductive tracts and related organs of humans and animals.

5. Methods and Medical Use of the Subject Medicament for Photodynamic Treatment of Conditions Affecting the Respiratory Tract and Related Organs.

The inventors have discovered that the intracorporeal medicaments disclosed herein are broadly applicable to improved photodynamic treatment of various conditions affecting the respiratory tract and related organs of humans and animals. The medicament can be applied, using conventional intracorporeal administration modes, directly or indirectly to, or substantially proximal to, tissues to be treated, including those of the lung and alveoli, bronchi, trachea, hypopharynx, larynx, nasopharynx, tear ducts, sinuses and nasal cavities. Such administration modes provide direct delivery of medicament to, into or substantially proximal to, tissues to be treated, or systemic delivery of medicament to, into or substantially proximal to, tissues to be treated.

Example indications include treatment for: Hyperplasia, Dysplasia and Neoplasia, Cancer. Inflammation and Infection of the Nasal Cavity, Paranasal Sinuses, Tear Ducts, Eustachian Tubes. Nasopharynx, Hypopharynx, Larynx, Trachea, Bronchi, Lung and Alveoli. These examples are provided for illustrative purposes as the present invention is not limited to the recited examples and includes other indications known to those skilled in the art.

In an example of a preferred embodiment of this method of treatment or medical use, the inventors have found that intratumoral injection of a medicament solution containing Rose Bengal at a concentration of approximately 10% W/V into tumor tissue, such as that of a lung tumor. followed by illumination of such tumor with green light in the 500-600 nm band, leads to controlled, localized photodynamic eradication of such tumors. The present invention, however, is not limited to this preferred embodiment, as other medicaments disclosed herein can also be used. Further, other formulations of the halogenated xanthenes as described herein have similar applications for the specific indications described herein, and for various other similar indications, including those related to therapeutic treatment of the respiratory tract and related organs of humans and animals.

6. Methods and Medical Use of the Subject Medicament for Photodynamic Treatment of Conditions Affecting the Circulatory System and Related Organs.

The inventors have discovered that the intracorporeal medicaments disclosed herein are broadly applicable to improved photodynamic treatment of various conditions affecting the circulatory system and related organs of humans and animals. The medicament can be applied, using conventional intracorporeal administration modes, directly or indirectly to, or substantially proximal to, tissues to be treated, including those of the heart, kidneys, liver and blood vessels. Such administration modes provide direct delivery of medicament to, into or substantially proximal to, tissues to be treated, or systemic delivery of medicament to, into or substantially proximal to, tissues to be treated.

Example indications include treatment for: Disease of Cardiac and Pericardial Tissues and Circulatory Tissues, including Arteries and Veins, including Plaques and Infections of such tissues such as Bacterial Endocarditis; and destruction of unwanted blood vessels, such as spider veins. These examples are provided for illustrative purposes, as the present invention is not limited to the recited examples and includes other indications known to those skilled in the art.

In an example of a preferred embodiment of this method of treatment or medical use, the inventors have found that per oesophageal administration of a medicament solution containing Rose Bengal at a concentration of approximately 10% W/V leads to transient elevation of serum levels of Rose Bengal; such circulating Rose Bengal can accumulate in lipophilic deposits, such as those in arterial plaques, and can thereby potentiate destruction of such plaques upon illumination with green light in the 500-600 nm band. The present invention, however, is not limited to this preferred embodiment, as other medicaments disclosed herein can also be used. Further, other formulations of the halogenated xanthenes as described herein have similar applications for the specific indications described herein, and for various other similar indications, including those related to therapeutic treatment of the circulatory system and related organs of humans and animals.

7. Methods and Medical Use of the Subject Medicament for Photodynamic Treatment of Conditions Affecting the Head and Neck.

The inventors have discovered that the intracorporeal medicaments disclosed herein are broadly applicable to improved photodynamic treatment of various conditions affecting the head and neck of humans and animals. The medicament can be applied, using conventional intracorporeal administration modes, directly or indirectly to, or substantially proximal to, tissues to be treated, including those of the head, neck, brain, eyes and ears. Such administration modes provide direct delivery of medicament to, into or substantially proximal to, tissues to be treated, or systemic delivery of medicament to, into or substantially proximal to, tissues to be treated.

Example indications include treatment for: Tumors or Resected Tumor Beds of Intra-cranial and other Head and Neck Tumors; Ophthalmic Tumors and other diseases, including Macular Degeneration and Diabetic Retinopathy; Metastatic Tumors, such as Metastases of Melanoma, Breast or Other Tumors to the Skin of the Head or Neck. These examples are provided for illustrative purposes, as the present invention is not limited to the recited examples and includes other indications known to those skilled in the art.

In an example of a preferred embodiment of this method of treatment or medical use, the inventors have found that intra-tumoral injection of a medicament solution containing Rose Bengal at a concentration of approximately 10% W/V into tumor tissue, such as that of a metastatic breast tumor, followed by illumination of such tumor with green light in the 500-600 nm band, leads to controlled, localized photodynamic eradication of such tumor. The present invention, however, is not limited to this preferred embodiment, as other medicaments disclosed herein can also be used. Further, other formulations of the halogenated xanthenes as described herein have similar applications for the specific indications described herein, and for various other similar indications, including those related to therapeutic or cosmetic treatment of the head and neck of humans and animals.

8. Methods and Medical Use of the Subject Medicament for Photodynamic Treatment of Conditions Affecting the Endocrine and Lymphoreticular Systems and Related Organs.

The inventors have discovered that the intracorporeal medicaments disclosed herein are broadly applicable to improved photodynamic treatment of various conditions affecting the endocrine and lymphoreticular systems and related organs of humans and animals. The medicament can be applied, using conventional intracorporeal administration modes, directly or indirectly to, or substantially proximal to, tissues to be treated, including those of the thyroid gland, the thalamus and hypothalamus, the pituitary gland, lymph nodes and lymphoreticular system. Such administration modes provide direct delivery of medicament to, into or substantially proximal to, tissues to be treated, or systemic delivery of medicament to, into or substantially proximal to, tissues to be treated.

Example indications include treatment for: Hyperplasia, Dysplasia and Neoplasia, Cancer, Inflammation and Infection of the Thyroid, Thalamus and Hypothalamus, Pituitary Gland, Lymph Nodes and Lymphoreticular system, including Graves' Disease. These examples are provided for illustrative purposes, as the present invention is not limited to the recited examples and includes other indications known to those skilled in the art.

In an example of a preferred embodiment of this method of treatment or medical use the inventors have found that intra-tumoral injection of a medicament solution containing Rose Bengal at a concentration of approximately 10% W/V into tumor tissue, such as that of a thyroid tumor, followed by illumination of such tumor with green light in the 500-600 nm band, leads to controlled, localized photodynamic eradication of such tumor. The present invention, however, is not limited to this preferred embodiment, as other medicaments disclosed herein can also be used. Further, other formulations of the halogenated xanthenes as described herein have similar applications for the specific indications described herein, and for various other similar indications, including those related to therapeutic treatment of the endocrine and lymphoreticular systems and related organs of humans and animals.

9. Methods and Medical Use of the Subject Medicament for Photodynamic Treatment of Conditions Affecting Various Other Tissues, Such as Connective Tissues and Various Tissue Surfaces Exposed During Surgery.

The inventors have discovered that the intracorporeal medicaments disclosed herein are broadly applicable to improved photodynamic treatment of various conditions affecting various other internal or external tissues of humans and animals, such as connective tissues and various tissue surfaces exposed during surgery. The medicament can be applied, using conventional intracorporeal administration modes, directly or indirectly to, or substantially proximal to, tissues to be treated. including those of tissue surfaces exposed during surgery, including endoscopic surgery or other endoscopic procedures. Such application modes provide direct delivery of medicament to, into or substantially proximal to, tissues to be treated or systemic delivery of medicament to, into or substantially proximal to, tissues to be treated.

Example indications include treatment for: Joint Inflammation, such as that of Arthritis; Resected Tumor Beds of Thoracic, Abdominal, or other Tumors; Metastatic Tumors, such as Metastases of Breast Tumors to the Skin; Tumors or Infections of the Pleura, Peritoneum or Pericardium; and various other substantially similar indications. These examples are provided for illustrative purposes, as the present invention is not limited to the recited examples and includes other indications known to those skilled in the art.

In an example of a preferred embodiment of this method of treatment or medical use, the inventors have found that intratumoral injection of a medicament solution containing Rose Bengal at a concentration of approximately 10% W/V into tumor tissue, such as that of a metastatic breast tumor, followed by illumination of such tumor with green light in the 500-600 nm band, leads to controlled, localized photodynamic eradication of such tumor. The present invention, however, is not limited to this preferred embodiment, as other medicaments disclosed herein can also be used. Further, other formulations of the halogenated xanthenes as described herein have similar applications for the specific indications described herein, and for various other similar indications, including those related to therapeutic or cosmetic treatment of conditions affecting various other tissues of humans and animals, such as connective tissues and various tissue surfaces exposed during surgery.

10. Methods and Medical Use of the Subject Medicament for Photodynamic Treatment of Conditions Related to Microbial, Viral, Fungal or Parasitic Infection.

The inventors have discovered that the intracorporeal medicaments disclosed herein are broadly applicable to improved photodynamic treatment of various conditions related to microbial, viral fungal or parasitic infection of humans and animals. The medicament can be applied, using conventional intracorporeal administration modes, directly or indirectly to, or substantially proximal to, tissues to be treated, including those of tissue surfaces exposed during surgery, including endoscopic surgery or other endoscopic procedures. Such administration modes provide direct delivery of medicament to, into or substantially proximal to, tissues to be treated, or systemic delivery of medicament to, into or substantially proximal to, tissues to be treated.

Example indications include treatment for: Bacterial and Antibiotic Resistant Bacterial Infection, including those caused by Gram Positives and Gram Negatives, *Streptomycetes, Actinomycetes, Staphylococci, Streptococci, Pseudomonas, Escherichia coli, Mycobacteria* and others; Infection caused by Filamentous Fungi and Non-filamentous Fungi like *Cryptosporidium, Histoplasma, Aspergillus, Blastomyces, Candida* and others; Parasitic Infection caused by Amoeba (including for use in lysing and killing amoeba in amoebic cysts), *Trichinella, Dirodfilaria* (Heart worm in dogs) and various other substantially similar indications. These examples are provided for illustrative purposes, as the present invention is not limited to the recited examples and includes other indications known to those skilled in the art.

In an example of a preferred embodiment of this method of treatment or medical use, the inventors have found that application of an aqueous solution containing Rose Bengal at a concentration of approximately 1 to 10 micromolar to antibiotic resistant *Staphylococcus aureus, Escherichia coli*, various other gram positive and gram negative bacteria, and various yeasts, followed by illumination with green light in the 500-600 nm band, leads to substantial or complete eradication of such microbes. The present invention, however, is not limited to this preferred embodiment, as other medicaments disclosed herein can also be used. Further, other formulations of the halogenated xanthenes as described herein have similar applications for the specific indications described herein, and for various other similar indications, including those related to therapeutic or cosmetic treatment of microbial, viral, fungal or parasitic infection of humans and animals.

TABLE 1

Chemical, Physical and Photochemical Properties of Some Example Halogenated Xanthenes.

| Compound | Substitution | | | | | MW (g) | $\lambda_{max}$ (nm) | | | $\alpha$ (cm$^{-1}$ · mol$^{-1}$ · L) | $\phi$ (triplet) MeOH | $\phi$ (singlet oxygen) | | |
|---|---|---|---|---|---|---|---|---|---|---|---|---|---|---|
| | X | Y | Z | R$^1$ | R$^2$ | | H$_2$O | EtOH | MeOH | | | H$_2$O | EtOH | MeOH |
| Fluorescein | H | H | H | Na | Na | 376 | 490 | 499 | 492 | 6.4 × 10$^4$ | 0.03 | 0.03 | 0.03 | 0.09 |
| 4',5'-Dichlorofluorescein | Cl | H | H | Na | Na | 445 | 502 | 511 | | | | 0.04 | 0.07 | |
| 2',7'-Dichlorofluorescein | H | Cl | H | Na | Na | 445 | 502 | 511 | | | | 0.04 | 0.07 | |
| 4,5,6,7-Tetrachlorofluorescein | H | H | Cl | H | H | 470 | 515 | | | 2.9 × 10$^4$ | | | | |
| 2',4',5',7'-Tetrachlorofluorescein | Cl | Cl | H | Na | Na | 514 | 510 | 520 | | | | 0.05 | 0.05 | |
| Dibromofluorescein | Br | H | H | Na | Na | 534 | 504 | 510 | | 1.4 × 10$^4$ | | 0.32 | 0.42 | |
| Solvent Red 72 | H | Br | H | H | H | 490 | | | 450 | 1.4 × 10$^4$ | | | | |
| Diiodofluorescein | I | H | H | Na | Na | 628 | 506 | 513 | | 5.8 × 10$^4$ | | 0.33 | 0.48 | |
| Eosin B | NO$_2$ | Br | H | Na | Na | 624 | 522 | | | 3.9 × 10$^4$ | | | | |
| Eosin Y | Br | Br | H | Na | Na | 692 | 517 | 523 | 527 | 9.1 × 10$^4$ | 0.28 | 0.32 | 0.57 | 0.39 |
| Ethyl Eosin | Br | Br | H | C$_2$H$_5$ | K | 714 | | 532 | | 1.1 × 10$^4$ | | | | |
| Erythrosin B | I | I | H | Na | Na | 880 | 528 | 532 | 529 | 9.1 × 10$^4$ | 0.62 | 0.69 | 0.63 | 0.62 |
| Phloxine B | Br | Br | Cl | Na | Na | 830 | 541 | 548 | 547 | 1.0 × 10$^5$ | | 0.40 | 0.63 | |
| Rose Bengal | I | I | Cl | Na | Na | 1018 | 547 | 557 | 556 | 1.0 × 10$^5$ | 0.76 | 0.86 | 0.75 | 0.76 |
| Rose Bengal Lithium Salt | I | I | Cl | Li | Li | 986 | | 559 | | | | | | |
| Rose Bengal Derivative I | I | I | Cl | C$_2$H$_5$ | (C$_2$H$_4$)$_3$NH | 1100 | | 563 | | | | | | 0.74 |
| Rose Bengal Derivative II | I | I | Cl | (C$_2$H$_5$)$_3$NH | (C$_2$H$_4$)$_3$NH | 1166 | | 559 | | | | | | 0.72 |
| 4,5,6,7-Tetrabromoerythrosin | I | I | Br | Na | Na | 1195 | | | | | | | | |

TABLE 2

Partition coefficients for several halogenated xanthenes and selected other photodynamic agents; $K_p$ is the ratio of equilibrium concentrations of agent in a lipophilic phase (n-octanol) contacted with an aqueous phase (phosphate buffered saline, PBS, pH = 7.4).

| Agent | $K_p$ |
|---|---|
| Phloxine B | 1.1 |
| Erythrosin B | 1.9 |
| Rose Bengal | 11.5 |
| Indocyanine Green | 99 |
| Porphyrin Agent P (PHOTOFRIN) | 0.1 |
| Porphyrin Agent Bo | 1.0 |
| Porphyrin Agent H (Hematoporphyrin Derivative) | 1.5 |
| Porphyrin Agent L | 11.5 |
| Porphyrin Agent Bp | >1000 |

TABLE 3

Per oesophageal administration using murine renal adenocarcinoma tumor model. Balb C Nude (nu/nu) mice were injected subcutaneously with approximately $1 \times 10^4$ renal adenocarcinoma cells, and tumors allowed to develop over a 2-3 week period. Mice were then administered a 10% Rose Bengal solution p.o. at a dose approximately equal to 50 mg/kg body weight. 3-20 hours after administration, the tumor and peritumoral area were illuminated using continuous wave green light (100 J/cm$^2$ of 532 nm light at an intensity of 200 mW/cm$^2$). Response was determined 24 hours after illumination by visual evaluation. Positive response was scored based on eschar formation selectively at the tumor site. No damage was noted in peritumoral tissues. "No Light" and "No Drug" controls (Light Dose = 0 J/cm$^2$ or no medicament, respectively) indicate that neither medicament alone (in the absence of illumination) nor light alone (in the absence of medicament) is capable of tumor destruction.

| Tumor Type | Medicament | Light Dose | Latency Period Between Drug Delivery and Light Delivery | No. Tumors Treated | No. Tumors With Positive Response | Cure Rate |
|---|---|---|---|---|---|---|
| Renal Adenocarcinoma | Rose Bengal | 100 J/cm$^2$ | 3 hr | 5 | 3 | 60% (3/5) |
| Renal Adenocarcinoma | Rose Bengal | 100 J/cm$^2$ | 20 hr | 9 | 7 | 78% (7/9) |
| Renal Adenocarcinoma | None | 100 J/cm$^2$ | — | 5 | 0 | 0% (0/5) |
| Renal Adenocarcinoma | Rose Bengal | 0 J/cm$^2$ | — | 2 | 0 | 0% (0/2) |

TABLE 4

Intratumoral injection using various murine tumor models. Subcutaneous tumors were injected with approximately 30 μL of a 10% Rose Bengal medicament solution or similar quantity of an indocyanine green (ICG) medicament. 24-48 hours after agent administration, the tumor and peritumoral area were illuminated using continuous wave green light (at a wavelength of 532 nm for Rose Bengal, 805 nm for ICG). The apparent cure rate was determined by measuring reoccurrence of the primary tumor at a period of approximately 2-3 weeks following illumination. "No Light" controls for Rose Bengal and ICG (Light Dose = 0 J/cm$^2$) indicate that medicament alone (in the absence of illumination) does not destroy the tumors tested.

| Tumor Type | Medicament | Average Tumor Size | Light Dose | No. Tumors Treated | No. Tumors Cured | Cure Rate |
|---|---|---|---|---|---|---|
| BNL/SV40 Liver Cell | Rose Bengal | 8 × 10 × 5 mm | 50 J/cm$^2$ | 8 | 2 | 25% (2/8) |
| Human Breast Adenocarcinoma (MCF-7) | Rose Bengal | 3 × 4 × 4 mm | 100 J/cm$^2$ | 2 | 2 | 100% (2/2) |
| Renal Adenocarcinoma | Rose Bengal | 2 × 3 × 3 mm | 100 J/cm$^2$ | 4 | 4 | 100% (4/4) |
| Renal Adenocarcinoma | Rose Bengal | 5 × 8 × 8 mm | 100 J/cm$^2$ | 4 | 2 | 50% (2/4) |
| Renal Adenocarcinoma | Rose Bengal | 2 × 3 × 3 mm | 0 J/cm$^2$ | 4 | 0 | 0% (0/4) |
| Renal Adenocarcinoma | ICG | 3 × 4 × 5 mm | 50 J/cm$^2$ | 4 | 0 | 0% (0/4) |
| Renal Adenocarcinoma | ICG | 3 × 4 × 5 mm | 0 J/cm$^2$ | 4 | 0 | 0% (0/4) |

This description has been offered for illustrative purposes only and is not intended to limit the invention of this application.

What is claimed as new and desired to be protected by Letters Patent is set forth in the appended claims.

We claim:

1. A method of treating human tissue comprising:
    applying an intracorporeal medicament comprising at least one halogenated xanthene into or proximate to said human tissue, wherein said halogenated xanthene is disodium 4,5,6,7-Tetrabromoerythrosin; and
    illuminating said human tissue with light having a wavelength of between approximately 500 and 600 unm to activate said halogenated xanthene present within or proximate to said tissue.

2. The method of claim 1 wherein said human tissue comprises the skin, the mouth and digestive tract, the urinary and reproductive tracts, the respiratory tract, the circulatory system, the head and neck, the endocrine and lymphoreticular systems, connective tissue, tissue surfaces exposed during surgery, and tissue with microbial, viral, or fungal infection.

* * * * *